(12) United States Patent
Iwashita

(10) Patent No.: US 11,427,208 B2
(45) Date of Patent: Aug. 30, 2022

(54) DRIVER CONDITION DETERMINATION APPARATUS, METHOD AND COMPUTER PROGRAM PRODUCT

(71) Applicant: Mazda Motor Corporation, Hiroshima (JP)

(72) Inventor: Yohei Iwashita, Aki-gun (JP)

(73) Assignee: MAZDA MOTOR CORPORATION, Hiroshima (JP)

( * ) Notice: Subject to any disclaimer, the term of this patent is extended or adjusted under 35 U.S.C. 154(b) by 10 days.

(21) Appl. No.: 17/035,767

(22) Filed: Sep. 29, 2020

(65) Prior Publication Data

US 2021/0107493 A1    Apr. 15, 2021

(30) Foreign Application Priority Data

Oct. 10, 2019 (JP) .............................. JP2019-186923

(51) Int. Cl.
*B60W 40/09* (2012.01)
*B60W 60/00* (2020.01)
(Continued)

(52) U.S. Cl.
CPC .......... *B60W 40/09* (2013.01); *B60W 40/105* (2013.01); *B60W 50/14* (2013.01);
(Continued)

(58) Field of Classification Search
CPC ............... B60W 40/105; B60W 50/14; B60W 60/0051; B60W 60/0057; B60W 2050/143; B60W 2050/146; B60W 2540/30; B60W 2520/10; B60W 2520/105; B60W 30/18145; B60W 30/18154; B60W 50/0097; B60W 2040/0818; B60W 2540/10; B60W 2540/18; B60W 2552/53; B60W 40/08; B60W 50/0098;
(Continued)

(56) References Cited

U.S. PATENT DOCUMENTS

2008/0006651 A1* 1/2008 Arakawa ............ B60H 1/00742
222/52
2009/0034796 A1* 2/2009 Johns ................... A61B 5/1103
382/103
(Continued)

FOREIGN PATENT DOCUMENTS

JP      2010-128649 A      6/2010
JP      2016045714    *    4/2016
(Continued)

OTHER PUBLICATIONS

Shinohara, K. et al., "Conscious Disturbance Attack while Driving", vol. 45, No. 6, Nov. 2014, 7 pages including English abstract.

*Primary Examiner* — Omar Casillashernandez
(74) *Attorney, Agent, or Firm* — Xsensus LLP

(57) ABSTRACT

A driver state determination apparatus includes circuitry configured to recognize whether a driver's voluntary function works normally and to recognize whether an involuntary function works normally. On condition that the driver's voluntary function does not work normally, the circuitry is configured to reduce a specified time required to recognize whether the involuntary function works normally.

16 Claims, 9 Drawing Sheets

(51) Int. Cl.
*B60W 40/105* (2012.01)
*B60W 50/14* (2020.01)

(52) U.S. Cl.
CPC .... *B60W 60/0051* (2020.02); *B60W 60/0057* (2020.02); *B60W 2050/143* (2013.01); *B60W 2050/146* (2013.01); *B60W 2540/30* (2013.01)

(58) Field of Classification Search
CPC ..... B60W 2540/223; B60W 2540/225; B60W 2540/229; A61B 5/0205; A61B 5/7275; A61B 5/746; A61B 5/18; A61B 5/168; A61B 2503/22; G08B 21/06; B60K 28/066; A61M 21/00; A61M 2021/0083; G08G 1/161; G08G 1/164
USPC ......................................................... 340/576
See application file for complete search history.

(56) References Cited

U.S. PATENT DOCUMENTS

| | | | | |
|---|---|---|---|---|
| 2016/0104050 | A1* | 4/2016 | Bogner | G08B 21/06 |
| | | | | 701/70 |
| 2021/0059615 | A1* | 3/2021 | Nakamura | G16H 50/30 |

FOREIGN PATENT DOCUMENTS

| | | |
|---|---|---|
| JP | 2019-079328 A | 5/2019 |
| JP | 2019-119373 A | 7/2019 |

\* cited by examiner

FIG. 7

| | | Phase1<br>HIGH VOLUNTARY FUNCTION | Phase2<br>LOW VOLUNTARY FUNCTION | Phase3<br>INVOLUNTARY FUNCTION |
|---|---|---|---|---|
| Case1 | DETERMINATION RESULT | NORMAL | NORMAL | — |
| | DETERMINATION CRITERION | DEFAULT | DEFAULT | NG IF ABNORMAL STATE CONTINUES FOR 2 SECONDS |
| Case2 | DETERMINATION RESULT | NORMAL | ABNORMAL | — |
| | DETERMINATION CRITERION | DEFAULT | DEFAULT | NG IF ABNORMAL STATE CONTINUES FOR 1 SECOND |
| Case3 | DETERMINATION RESULT | ABNORMAL | ABNORMAL | — |
| | DETERMINATION CRITERION | DEFAULT | REDUCE THRESHOLD FOR ABNORMAL DETERMINATION | NG IF ABNORMAL STATE CONTINUES FOR 0.5 SECOND |

DRIVER CONDITION DETERMINATION APPARATUS, METHOD AND COMPUTER PROGRAM PRODUCT

CROSS-REFERENCE TO RELATED APPLICATION

The present application claims priority to JP 2019-186923, filed Oct. 10, 2019, the entire contents of which are incorporated herein by reference.

TECHNICAL FIELD

A technique disclosed herein relates to determination of a state of a driver who drives a vehicle, e.g., an automobile.

BACKGROUND ART

Recently, development of automated driving systems has been promoted.

The present applicant considers that there are two types of automated driving systems.

A first type relates to a system that helps an automobile to transport an occupant to a destination without a need for an operation by a driver, i.e., fully-automated travel of the automobile. For example, Patent document 1 discloses an automated driving technique that shifts primary driving responsibility to the automobile when the occupant performs a specified operation.

The second type relates to an automated driving system that is designed to "provide environment that makes automobile driving enjoyable" that is, with an assumption that the driver is responsible for driving. In the automated driving system of the second type, when a situation occurs that the driver is no longer able to drive normally, e.g., suddenly suffers from an illness, falls asleep, and the like, the automobile executes automated driving instead of the occupant.

Patent document 2 discloses a technique of determining appropriateness of a vehicle driving state by the driver on the basis of a driving posture and an eye-opening amount of the driver that are acquired from an analysis result of a video captured by an imaging section. Patent document 3 discloses a technique of setting a determination criterion for a degree of consciousness of the driver and determining a conscious state of the driver on the basis of detected behavior of the driver's head and the set determination criterion. In Non-Patent document 1, a case where the driver had a conscious disturbance attack while driving is discussed.

PRIOR ART DOCUMENTS

Patent Documents

[Patent document 1] JP-A-2019-119373
[Patent document 2] JP-A-2019-79328
[Patent document 3] JP-A-2010-128649

Non-Patent Documents

[Non-Patent document 1] Shinohara and 7 others (2014) Untenchu ni ishiki shogai Kossa wo hassho shita shorei no kentou [Conscious disturbance attack while driving]. *Transactions of Society of Automotive Engineers of Japan*, 45(6), 1105-1110.

SUMMARY OF THE DISCLOSURE

For example, as disclosed in Patent document 2, the following technique has been known. In the case where the driver becomes no longer able to drive and hunches over, it is determined that there is a high probability that the driver suffers from dysfunction or the illness and thus the driving state of the driver is inappropriate. For example, in Patent document 3, motion of the head or a body of the driver is recognized. Then, based on a recognition result, a so-called dead man determination is made. In the case where a state of the driver who can no longer continue driving is recognized, instead of the driver, the technique allows the host vehicle to be directed to a safe place.

In such a case, it is extremely important to discover occurrence of abnormality to the driver, in particular, an outbreak of the dysfunction or the illness to the driver as soon as possible from perspectives of improvement in a life-saving rate of the driver and safety of surrounding environment. In particular, in the second type of automated driving system, the driver is primarily responsible for driving. Thus, it is extremely important to discover the abnormality of the driver as soon as possible in order to provide an ease of mind and safety to the driver himself/herself and others.

A technique disclosed herein has been made in view of such points and therefore has a purpose of reducing a time required for an abnormality determination of a driver as much as possible.

One or more embodiments disclosed herein is targeted for a driver state determination apparatus that is mounted on an automobile and that includes: a voluntary function recognition section that recognizes whether a voluntary function of a driver works normally in order to detect a prediction of an outbreak of abnormality of the driver; and an involuntary function recognition section that recognizes whether an involuntary function works normally on the basis of a fact that the involuntary function remains in an abnormal state for a specified time or longer. The driver state determination apparatus is configured to reduce the specified time that is required to recognize whether the involuntary function recognition section works normally in the case where it is recognized that the voluntary function does not work normally.

High and low voluntary functions and the recognition of whether the involuntary function works normally in the apparatus according to embodiments are directed to saving life and securing safety by accelerating the abnormality determination of the driver, and include aspects such as estimation and determinations by apparatus hardware. In addition, the recognition in the apparatus according to embodiments is a different concept from a concept that a healthcare professional examines a human body to determine whether the body functions normally.

According to this configuration, in the case where the prediction of the abnormality of the driver is detected on the basis of whether the voluntary function of the driver works normally and it is recognized that the voluntary function of the driver does not work normally, the specified time that is required to recognize whether the involuntary function recognition section functions normally is reduced. As a result, compared to a case where the abnormality of the driver is determined only on the basis of the involuntary function, a time required for the determination of the abnormality of the driver can be reduced while accuracy of the determination of the abnormality is secured as high as possible.

As an aspect of the driver state determination apparatus, the voluntary function recognition section may include: a high voluntary function recognition section that recognizes whether a high voluntary function that is a relatively high voluntary function works normally; and a low voluntary function recognition section that recognizes whether a low voluntary function that is a lower voluntary function than the high voluntary function works normally. In the case where it is recognized that the high voluntary function recognition section does not function normally, determination criteria of the low voluntary function recognition section and/or the involuntary function recognition section may be changed. Meanwhile, in the case where it is recognized that the low voluntary function recognition section does not function normally, the determination criterion of the involuntary function recognition section may be changed.

According to this configuration, before the involuntary function is impaired, a condition for the determination of the abnormality (for example, a reduction in a determination time) is changed according to a combination of normality/abnormality of the high voluntary function and the low voluntary function. As a result, it is possible to further accelerate the determination of the abnormality of the driver and to increase accuracy of the prediction used for the determination of the abnormality.

As an aspect of the driver state determination apparatus, in the case where it is recognized that at least one of the high voluntary function and the low voluntary function does not work normally, an actuation method by an actuation execution section that executes actuation for the driver may be changed.

Just as described, when the driver is notified or warned, it is possible to increase the accuracy of the determination of the abnormality of the driver and to urge the driver to act safely.

As it has been described so far, according to the technique disclosed herein, it is possible to accelerate the determination of the abnormality of the driver.

BRIEF DESCRIPTION OF THE DRAWINGS

FIG. 7 is a table for illustrating the operation of the driver state determination apparatus.

DETAILED DESCRIPTION

Merits of a technique of the present disclosure are fully appreciated particularly when such a technique is adopted for the second type of automated driving system, i.e., an automated driving system with an assumption that a person drives an automobile (hereinafter referred to as a driver-led automated driving system).

Fully-automated driving promises freedom of mobility of elders and is an extremely important advancement. Meanwhile, embodiments disclosed herein considers that the fully-automated driving is not the only automated driving system (technology) useful for next generation.

The present applicant considers that, with an idea centered on how persons should be, realization of life fulfilled by free mobility is an ideal of a next-generation personal car for which automated driving technique is adopted. In other words, the present applicant considers that a technique for improving mobility and capability of a person while providing pleasure to help the person to be back on a natural human state is requested. The present applicant also considers that revitalization of mind and a body of the person by enjoyable automobile driving is a natural effect of the automobile. When driving, the person exerts his/her capability and feels active while the automobile is prepared for appropriate handling of a state by grasping motion of itself, surrounding environment, and the like, that is, stays present to a sense of the person. As a result, the person in the automobile naturally senses motion of the automobile and feels safe in the automobile without a sense of discomfort. When the person owns such an automobile and has such "fulfilled satisfaction" that the person wants to drive the automobile as long as possible, the person obtains extreme joyfulness of driving. Meanwhile, the automobile provides the person with safety and a sense of ease. This is an idea of safety considered by the present applicant, and this is how the automated driving technique by the present applicant is used.

Figure 1:
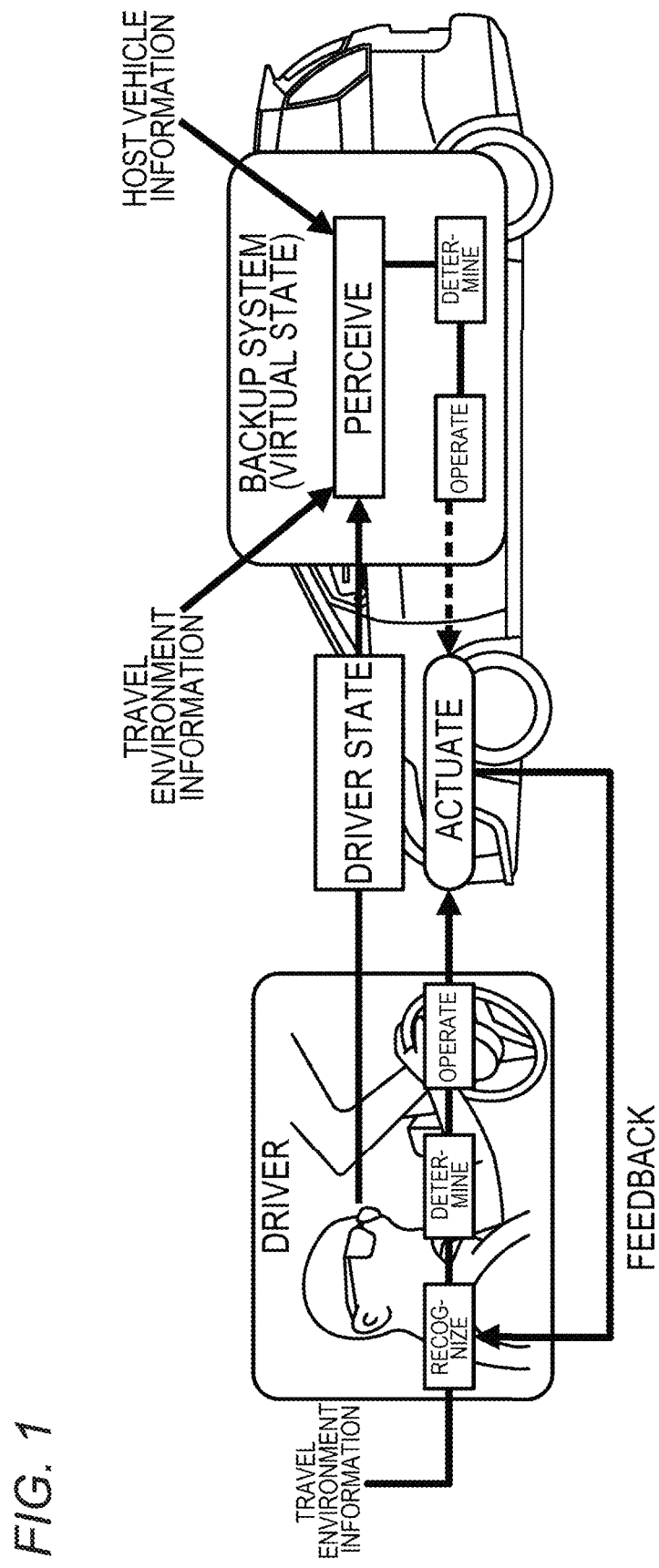
FIG. 1 is a conceptual view for illustrating a driver-led automated driving system.

FIG. 1 is a view that schematically illustrates the above overview.

As illustrated in FIG. 1, a driver recognizes travel environment information of the automobile through five senses including eyesight and hearing. The driver determines how to maneuver the automobile on the basis of the recognized travel environment information, and operates a steering wheel, an accelerator, a brake pedal, or the like on the basis of a determination result. For example, in the case where the driver determines a possibility of a collision with an external object or departure from a lane, the driver decides a travel route (for example, a target location, acceleration/deceleration, or the like) to avoid such a situation, and performs an operation therefor. Consequently, various actuators AC (see FIG. 5B) in the automobile are started, and operation thereof is reflected to travel of the automobile. The driver accepts a vehicle travel state as a result of such an operation as feedback, makes a determination on the basis of the feedback and the recognition result of the travel environment information, and performs an operation on the basis of the determination. The driver repeats such maneuvers. Here, the travel environment information is information on travel environment of the automobile and includes external environment information of a host vehicle. For example, the external environment information includes information on a sign and a building, information on stationary objects including road information such as a median strip and a center poll, and information on mobile objects such as another vehicle (an automated four-wheeled vehicle), an automated two-wheeled vehicle, a bicycle, and a pedestrian. Examples of the actuators AC include an engine system 81, a brake system 82, a steering system 83, and a transmission (see FIG. 5B).

In regard to the automobile on which the driver-led automated driving system is mounted, the driver usually maneuvers the automobile (in a normal state). In the normal state, the driver-led automated driving system grasps states of the host vehicle and the external environment and the state of the driver so as to execute virtual driving behind maneuvering by the driver. In other words, the driver-led automated driving system is operated as a backup system. More specifically, similar to the driver, the driver-led automated driving system recognizes the travel environment information, and also recognizes the state of the host vehicle and the state of the driver. Based on the above recognition results, the driver-led automated driving system determines how to move the automobile, and decides target motion of the automobile in parallel with maneuvering by the driver. Then, when determining that the driver suffers from dysfunction or the illness, the driver-led automated driving system operates the host vehicle instead of the driver so as to secure safety of the host vehicle and the surrounding environment, and also complements a declined function of the driver among functions such as perception, determination, and operation.

The driver-led automated driving system is designed to be operated as described above as a precondition. Thus, it is extremely important to discover the outbreak of the abnormality, such as the declined function, the dysfunction, or the illness, to the driver (hereinafter referred to as driver abnormality) as soon as possible.

Figure 2:
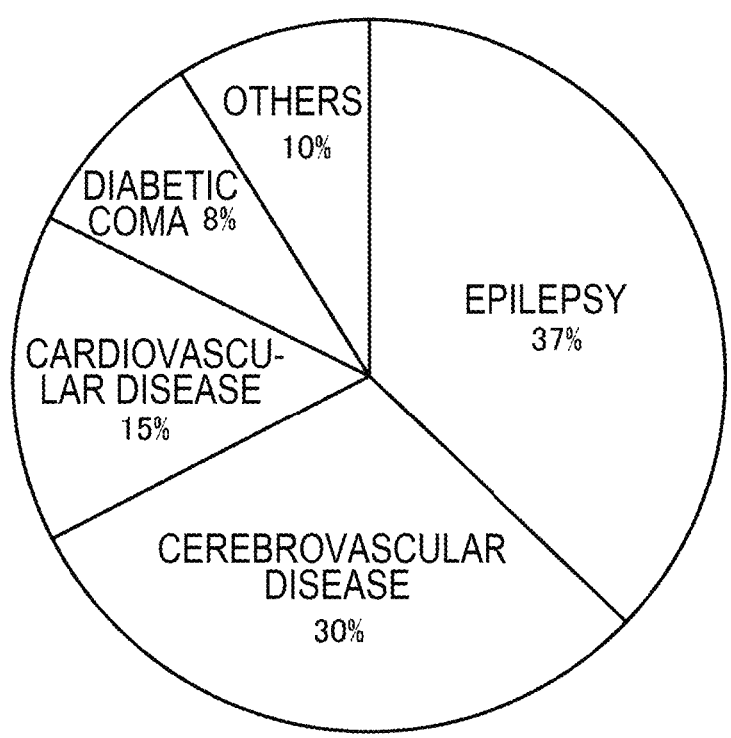
FIG. 2 is a graph illustrating a breakdown of illnesses and an influences on driving.

The driver state is largely categorized into a normal healthy state and an abnormal state where the driver suffers from the dysfunction or the illness. The normal state includes a flow state where the driver is concentrated on driving at a maximum, a concentrated driving state, a relaxed driving state, an inattentive driving state, a desultory driving state, a declined awakening state, and a drowsy state in a descending order of a degree of awareness. As discussed in Non-Patent document 1 illustrated in FIG. 2, representative examples of the illnesses that cause conscious disturbance while driving are epilepsy, apoplexy, myocardial infarction, and hypoglycemia.

Figure 3:
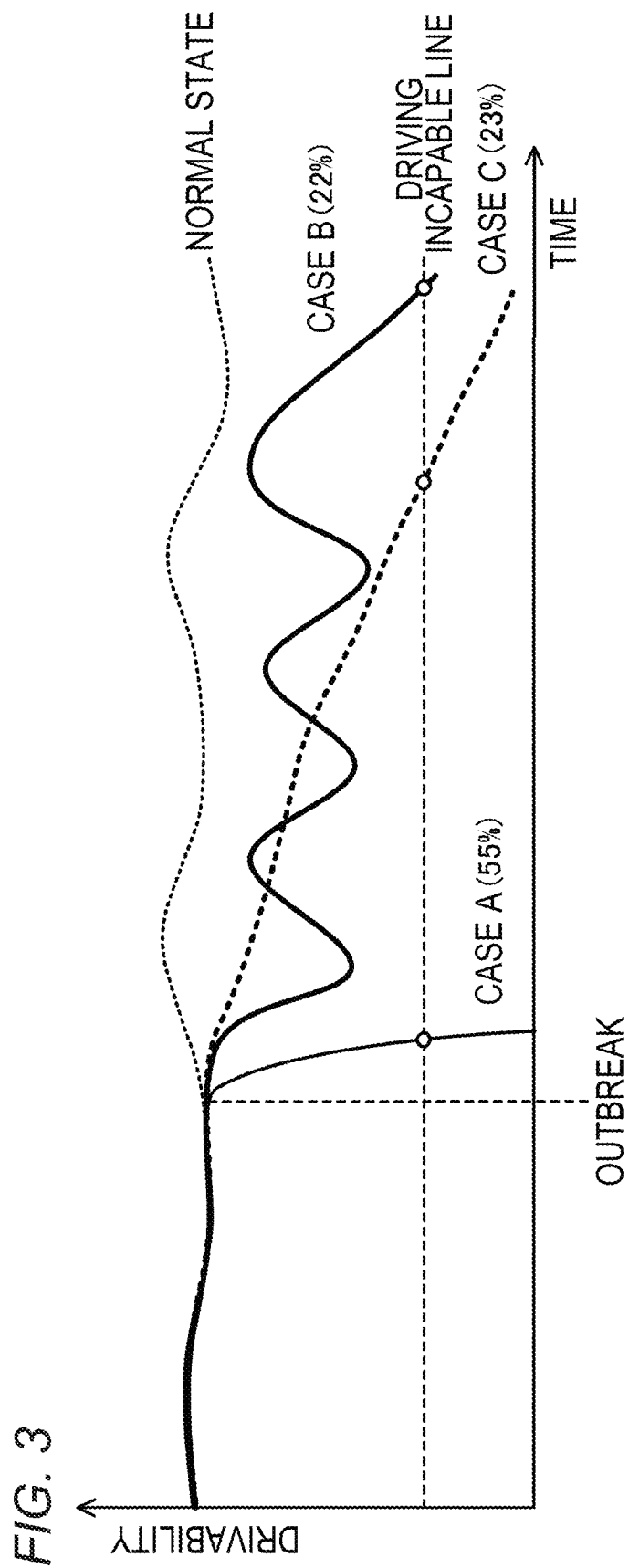
FIG. 3 is a chart illustrating temporal changes in a decline in a driver state after an outbreak of the illness.

The inventor has determined that a change of a driver state from the normal state (the healthy state) to a state where the driver can no longer drive due to the conscious disturbance may be categorized into three patterns. FIG. 3 illustrates the three patterns (cases) of a decline in the driver state. In FIG. 3, a vertical axis represents a change in drivability with respect to time on a horizontal axis. In FIG. 3, when a pattern falls below a driving incapable line, the driver is assumed to be no longer able to drive.

In FIG. 3, a case A is a pattern that, when the driver suffers from the illness, the driver becomes unconscious without prior warning. The case A in approximately 55% of all cases. The case A is a pattern that is frequently observed in cases of epilepsy, and is also observed in some cases of myocardial infarction and a brain disorder. A case B is a pattern that the driver does not lose consciousness all at once. In the case B, the driver state is gradually declined as a whole while the driver feels something is wrong, that is, a relatively good state and a bad state repeatedly occur. The case B occurs at a rate of approximately 22% of all the cases and is frequently observed in the cases of a brain disorder. A case C is a pattern that, when the driver suffers from the illness, the driver state is slowly and gradually declined, and the driver eventually loses consciousness. The case C occurs at a rate of approximately 23% of all the cases and is frequently observed in cases of hypoglycemia.

For all of these three cases, with a current technical standard for detecting the driver state in a level adopted for the normal automobile, the outbreak of the illness can only be recognized after the driver state reaches the driving incapable line. This is because it is difficult to determine whether the driver is in a state of being healthy but looming, a state with accumulated fatigue, or a state with the outbreak of the illness. In addition, even when the driver is in the healthy state, the driver may close his/her eyes, and a posture of the driver may become imbalance. Thus, it is necessary to determine the abnormality of the driver under a condition that a state of imbalance posture and a state of the driver who keeps his/her eyes closed or open continue for a specified time. That is, the related art has a problem of requiring a long time for determination when it is attempted to accurately discover the outbreak of the illness, and also has a problem of increased frequency of an erroneous determination when it is attempted to reduce the time required for the determination of the illness.

In view of the above, the inventor focused on a mechanism of loss of the functions of the driver in a sequential order. In other words, the inventor paid attention to a prediction of the outbreak of the illness, and considered to determine the outbreak of the driver abnormality by using a detection result of such a prediction. As a result, it is possible to promptly and accurately determine the outbreak of the driver abnormality.

In general, as a method for determining the driver abnormality, such a technique has been known to detect the outbreak of the abnormality of a function that is established regardless of the driver's intention, that is, an involuntary function. As a method for detecting the abnormality of the involuntary function, such a method has been known to analyze the imbalance driving posture of the driver and the eye-opening amount of the driver on the basis of a video captured by an imaging section, so as to determine the outbreak of the illness of the driver. When focusing on brain functions, on contrary to the involuntary function, a voluntary function of a person exists. Recently, techniques of detecting this voluntary function have been developed individually. The inventor of the present application further investigated classification based on this voluntary function while focusing on the brain functions. More specifically, the inventor classified the voluntary function into: a voluntary function that was similar to a function of maintaining life and was processed in a barely conscious area (herein referred to as a "low voluntary function"); and a voluntary function that was processed in a conscious area (hereinafter referred to as a "high voluntary function") in comparison with the low voluntary function. For example, the high voluntary function is a function that has an impact on whether so-called "driving while forecasting possible occurrence of something" can be performed. With such classification, the inventor acquired knowledge that, after the outbreak of the driver abnormality, the high voluntary function was likely to be lost first, and the low voluntary function was likely to remain to the last.

Figure 4:
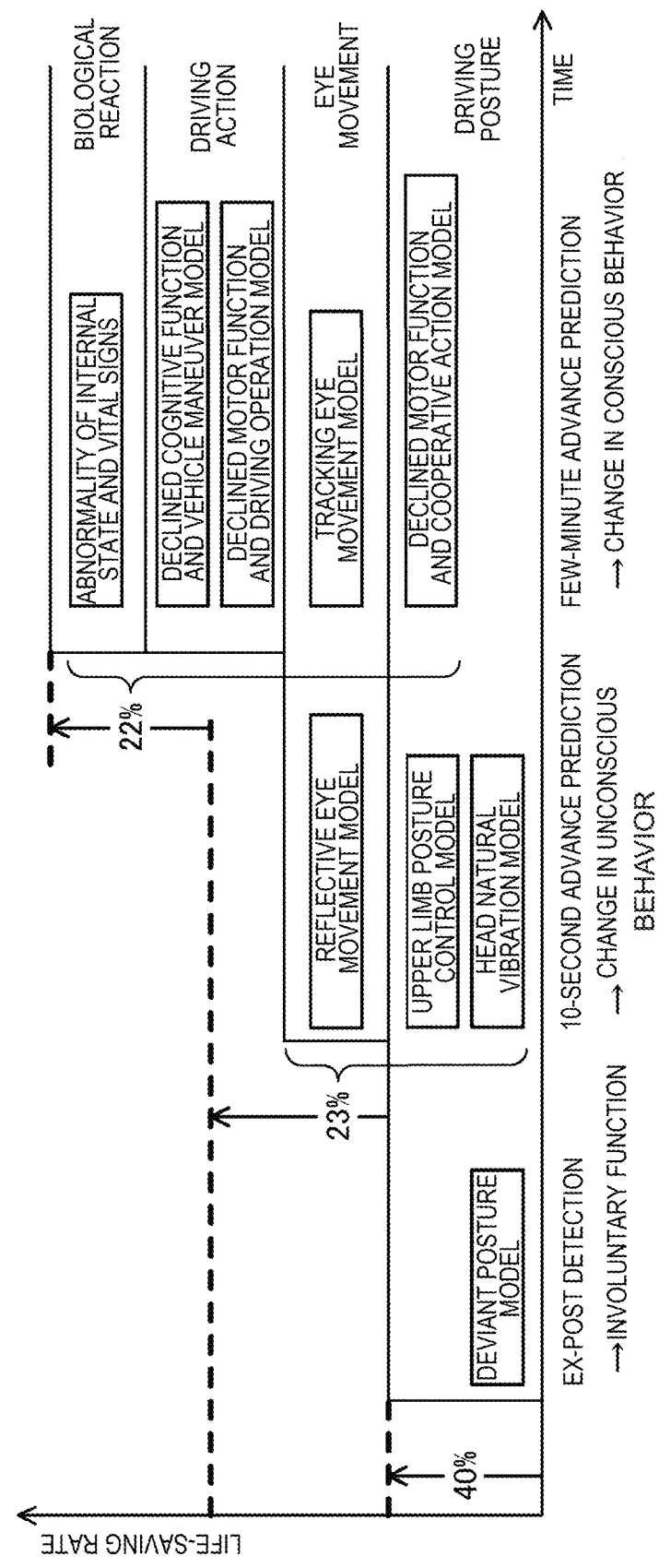
FIG. 4 is a chart for illustrating ex-post detection and detection of predictions.

FIG. 4 is a conceptual chart illustrating when and what types of the predictions and events occur in relation to the driver abnormality that shows behaviors as indicated in the cases B, C in FIG. 3 and also illustrating a relationship between each of the predictions and the events and a life-saving rate at a time point when the prediction or the event occurs. In FIG. 4, time goes back in a right direction of a time axis from timing at which the driver loses consciousness.

In a right portion, FIG. 4 illustrates examples of the predictions (hereinafter referred to a few-minute advance predictions) that are detected a few minutes before the driver abnormality occurs and the driver becomes no longer able to drive. In the few-minute advance predictions, particularly, relatively high conscious behavior of the driver, that is, the high voluntary function is likely to be changed. Thus, in order to detect onset of the few-minute prediction, it is focused on whether the high voluntary function works normally. The change in the high voluntary function is detected on the basis of indices that include a saccade reaction against saliency and frequency of rapid operations, for example.

More specifically, for example, as the few-minute advance predictions of driving action, a cognitive function and a motor function tend to decline. For example, as the few-minute advance prediction of eye movement, trackability of eyes tend to be declined. For example, as the few-minute advance prediction of the driving posture, the motor function tends to be declined. For example, as the few-minute advance predictions of a biological reaction, an internal state and vital signs of the driver tend to become abnormal, which causes an abnormal heart rate of the driver. Thus, by determining the abnormality of the vital sign or the decline in any of the various functions described above, it is possible to detect the few-minute advance prediction. In order to detect the few-minute advance prediction, for example, a vehicle maneuver model, a driving operation model, a tracking eye movement model, a cooperative action model, and the like can be used. All of the few-minute advance predictions do not always occur, and only one or some of the few-minute advance predictions may occur. An example of a specific detection method of the few-minute advance prediction will be described below. At a stage of the few-minute advance prediction, the driver may be in a state capable of continuing driving. At the stage of the few-minute advance prediction, the life-saving rate is approximately 85%.

In a center portion, FIG. 4 illustrates examples of the predictions (hereinafter referred to 10-second advance predictions) that are detected several seconds or a dozen seconds before the driver abnormality occurs and the driver becomes no longer able to drive. In the 10-second advance prediction, substantially unconscious behavior of the driver is likely to be changed. That is, at a stage of the 10-second advance prediction at which a certain time elapses from the outbreak of the driver abnormality and which is a relatively close stage to the driving incapable line, in addition to the high voluntary function, the low voluntary function is also likely to be changed. Thus, in order to detect the onset of the 10-second advance prediction, whether the low voluntary function works normally is determined. The detection of whether the low voluntary function works normally can be made on the basis of indices that include vestibulo-ocular reflex, constancy of a head, wobbling of steering, and stability of a speed, for example. For example, the 10-second advance prediction can be detected by using a reflective eye movement model, an upper limb posture control model, a head natural vibration model, a detection result of vehicle behavior, and the like.

More specifically, in the 10-second advance prediction, for example, in the case where vestibulo-ocular reflex action becomes abnormal, the driver is likely not to be able to keep his/her eyesight at a fixed position (for example, to the front) with his/her head rocking. In addition, in the 10-second advance prediction, for example, the constancy of the head tends to become abnormal. As the abnormality of the constancy of the head, for example, when the automobile rocks, the constancy of the head cannot be maintained, and the head rocks more than necessary. In addition, in a case of muscle stiffing, motion of the head with respect to rocking of the automobile is significantly reduced in comparison with that of a healthy person. In the 10-second advance prediction, for example, steering tends to wobble, or the speed tends to be unstable. Thus, the 10-second advance prediction can be detected on the basis of the change in the state of head or the eyes of the driver or on the basis of the change in the behavior of the automobile. All of the 10-second advance predictions do not always occur, and only one or some of the 10-second advance predictions may occur. An example of a specific detection method of the 10-second advance prediction will be described below. At the stage of the 10-second advance prediction, the life-saving rate is approximately 63%.

In a left portion, FIG. 4 illustrates an example in which loss of consciousness of the driver is detected ex-post facto (hereinafter referred to as ex-post detection). As described above, the ex-post detection can be made on the basis of the imbalance driving posture of the driver, a long-term eye closing state/continuity of the eye opening state, absence of a pupil reaction, or the like. While normal driving, the imbalance driving posture of the driver or eye closing/eye opening temporarily also occurs. Thus, in the ex-post detection, the abnormality is usually determined on the basis of whether such a state continues for a specified time. For this reason, there is a problem of an elongated time being required to determine the abnormality. For example, a deviant posture model, an image capturing result of the driver by a camera, or the like can be used for the ex-post detection.

Figure 5A:
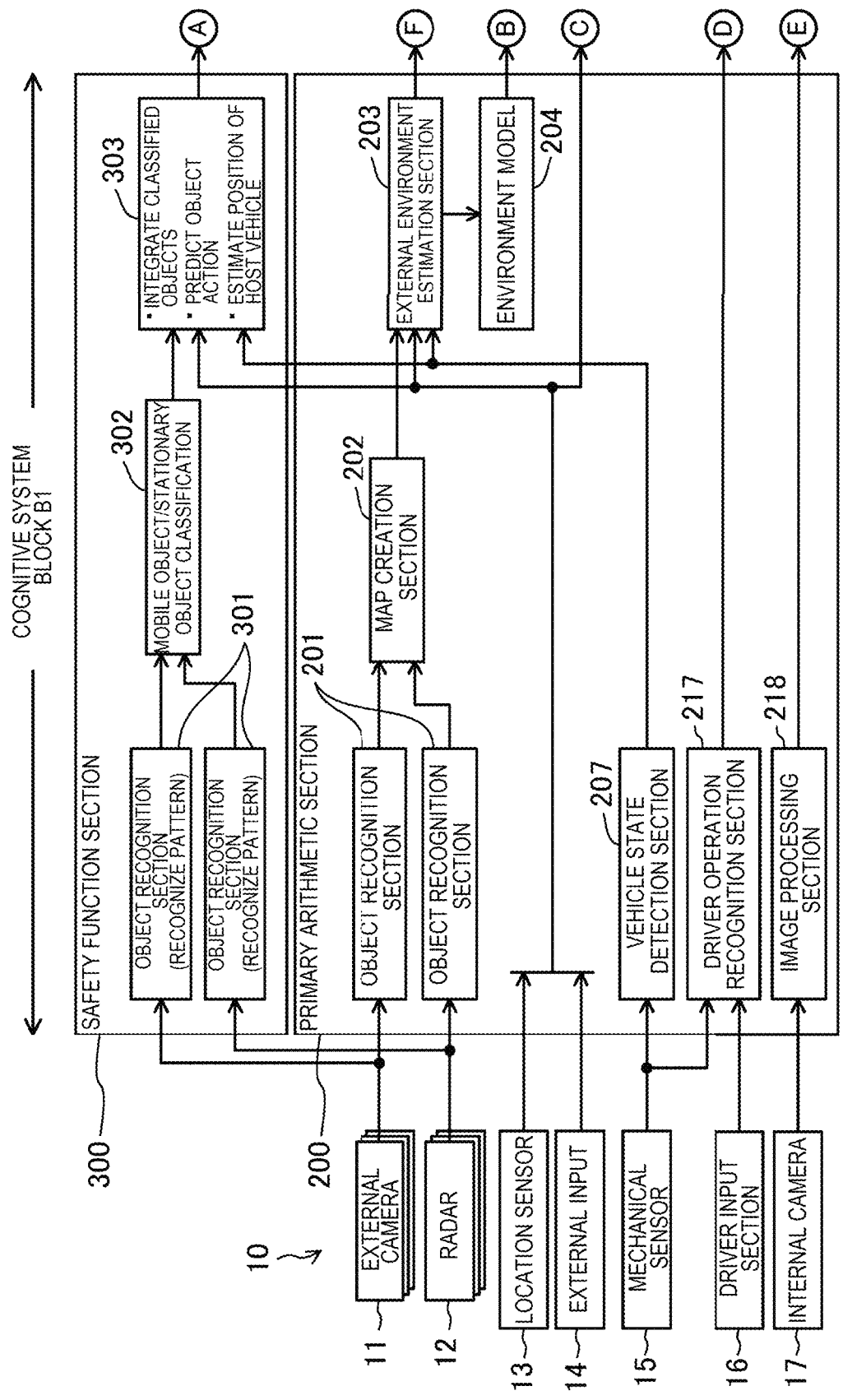
FIG. 5A is a block diagram illustrating a functional configuration of an automotive arithmetic system.
Figure 5B:
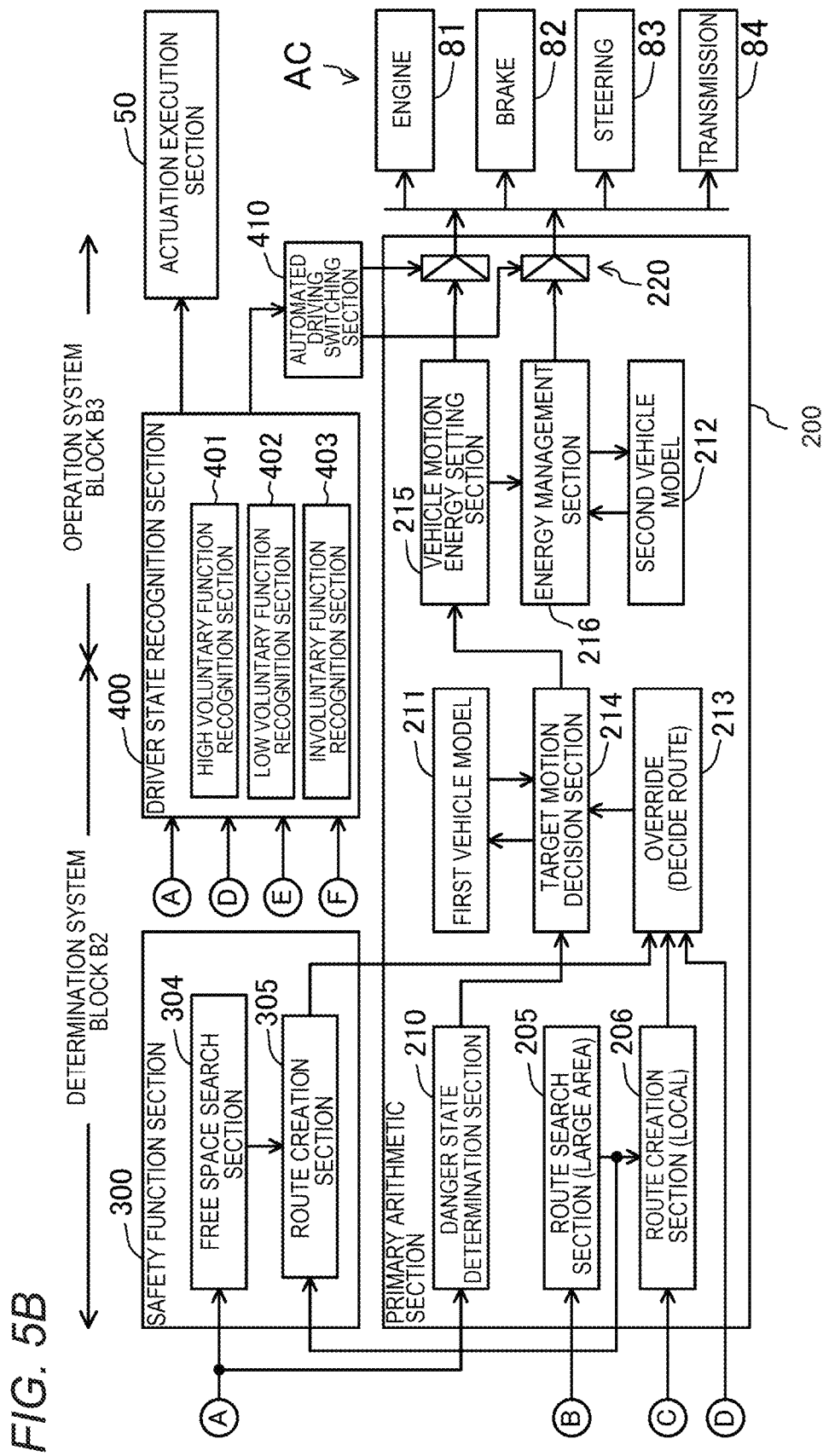
FIG. 5B is a block diagram illustrating the functional configuration of the automotive arithmetic system.

FIG. 5A and FIG. 5B are block diagrams, each of which illustrates a functional configuration example of a driver-led automated driving system control unit (CU) that has a driver state determination apparatus according to an embodiment. In the following description, FIG. 5A and FIG. 5B will collectively be referred to as FIG. 5.

The driver-led automated driving system CU according to the present disclosure (hereinafter simply referred to as an automated driving system CU) is functionally divided into a cognitive system block B1, a determination system block B2, and an operation system block B3. Optionally, the automated driving system CU may include a processor 835 and other circuitry in system 800 of FIG. 8, which may be implemented as a single processor-based system, or a distributed processor based system, including remote processing, such as cloud based processing.

The cognitive system block B1 is configured to perceive external environment and internal environment of the automobile (including the driver state). The determination system block B2 is configured to determine various states, various situations, and the like on the basis of a recognition result by the cognitive system block B1, so as to determine the operation of the automobile. The operation system block B3 is configured to specifically generate signals/data to be transmitted to the actuators on the basis of the determination in the determination system block B2.

The automated driving system CU includes: (1) a primary arithmetic section 200 that includes the cognitive system block B1, the determination system block B2, and the operation system block B3 to implement automated driving during normal driving; and (2) a safety function section 300 that has a function to complement the cognitive system block B1 and the determination system block B2 in the primary arithmetic section 200.

The automated driving system CU receives data as an input signal from information acquisition means 10 that acquires information on the internal/external environment of the automobile. The automated driving system CU may also receive information as an input signal from a system or a service connected to an external network (for example, the Internet or the like) like cloud computing (described as "EXTERNAL INPUT" in FIG. 5).

Examples of the information acquisition means 10 are: (1) plural vehicle exterior cameras 11, each of which is provided to a body or the like of an automobile 1 to capture an image of the exterior environment of the automobile; (2) plural radars 12, each of which is provided to the body or the like of the automobile 1 to detect an object, a sign, and the like on the outside of the vehicle; (3) a location sensor 13 that includes a positioning system such as the GPS; (4) external input 14 from the external network described above or the like; (5) a mechanical sensor 15 that is attached to the automobile 1; (6) a driver input section 16 that accepts an input operation by the driver; and (7) an internal camera 17 that is provided to a rear-view mirror, a dashboard, or the like of the automobile 1. The external cameras 11 may include an image sensor that takes fixed and/or moving images in the visual spectrum and/or non-visual ranges such as infrared and ultraviolet. The radars 12 may include short-range radars, SRR, that operate, e.g., in the 20 GHz to 27 GHz range, long range radars, LRR, operating, e.g., in the 76 to 81 GHz range, as well as Lidar that operates in at least one of ultraviolet, visible, and near infrared spectrums using lasers having a principle wavelength, for example, in a range of 500 nm to 1000 nm. The external input may include navigation data. The internal camera 17 may capture images of the posture, facial expression, the eye opening state, and a line of sight of the driver, the internal environment of the automobile, and the like. The mechanical sensor 15 includes a vehicle speed sensor that detects an absolute speed of the automobile 1. The driver input section 16 includes a sensor that detects an operation of any of various operation targets, such as an accelerator pedal, a brake pedal, the steering wheel, or various switches, by the driver. The driver input section 16 includes, for example: an accelerator operation amount sensor that detects a depression amount of the accelerator pedal; a steering angle sensor that detects a rotation angle (a steering angle) of the steering wheel; and a brake sensor (a hydraulic pressure sensor) that detects a depression amount of the brake pedal. The driver input section 16 may also include biological sensors to monitor vital signs of the driver, e.g., heart rate.

—1-1. Primary Arithmetic Section (1)—

A description will herein be made on a configuration of the primary arithmetic section 200 with exemplary creation of a route using deep learning by the primary arithmetic section 200.

The cognitive system block B1 and the determination system block B2 in the primary arithmetic section 200 execute processing by using any of the various models that are developed by deep leaning using a neural network. When the processing is executed by using such a model, driving may be controlled on the basis of a comprehensive determination on the vehicle state, the external environment of the automobile, the driver state, and the like. That is, driving may be controlled by synchronizing a large volume of the input information in real time.

More specifically, the primary arithmetic section 200 includes an object recognition section 201 that recognizes an external object, a map creation section 202, an external environment estimation section 203, an external environment model 204, a route search section 205, a route creation section 206, and a vehicle state detection section 207.

The object recognition section 201 receives the image (including the video) of the outside of the automobile that is captured by the external camera 11 and recognizes the external object on the basis of the received image. A recognition result of the object recognition section 201 is transmitted to the map creation section 202.

The map creation section 202 divides a surrounding area of the host vehicle into plural areas (for example, front, right, left, and rear), and executes processing to create a map of each of the areas. More specifically, the map creation section 202 integrates target information recognized by the external camera 11 and object information recognized by the radar 12, and reflects the integrated information to the map of each of the areas.

The map created by the map creation section 202 and a detection result of the vehicle state detection section 207 are used when the external environment estimation section 203 estimates the exterior environment of the automobile in image recognition processing using deep learning. More specifically, the external environment estimation section 203 executes the image recognition processing that is based on the external environment model 204 developed by using deep learning, and creates a 3D map that represents the exterior environment. In deep learning, a deep neural network (DNN) is used. As the DNN, for example, a convolutional neural network (CNN) is available.

More specifically, in the external environment estimation section 203, (1) the maps of the areas are joined to create an integrated map that shows surroundings of the host vehicle, (2) changes in a distance between the host vehicle and a mobile object in the integrated map as well as changes in a direction and a relative speed of the mobile object are predicted, and (3) results thereof are embedded in the external environment model 204. Further specifically, in the external environment estimation section 203, (4) a location of the host vehicle on the integrated map is estimated from a combination of high-precision map information that is acquired from inside or outside of the automobile, location information acquired by the GPS or the like, vehicle speed information, and six-axis information, (5) cost for the above-described route is calculated, and (6) a result thereof and motion information of the host vehicle that is acquired from the various sensors are embedded in the external environment model 204. With the above processing (1) to (6), the external environment estimation section 203 updates the external environment model 204 as needed. The external environment model 204 is used when the route creation section 206, which will be described below, creates the route.

The signal from the positioning system such as the GPS in the location sensor 13 and car navigation data from the external network of the external input 14, for example, are transmitted to the route search section 205. The route search section 205 searches for an extensive route for the vehicle by using the signal from the positioning system such as the GPS of the location sensor 13 and the navigation data from the external network of the external input 14, for example.

The route creation section 206 creates the travel route of the vehicle on the basis of the above-described external environment model 204 and the output of the route search section 205. For example, the route creation section 206 scores safety, fuel economy, and the like, and creates at least one travel route with a low score. Alternatively, the route creation section 206 may create the travel route that is based on plural perspectives such as the above travel route and a travel route that is adjusted according to the operation amount by the driver. Information on the travel route that is created by this route creation section 206 is included in external environment data.

—1-2. Safety Function Section—

A description will herein be made on a configuration of the safety function section 300 with exemplary creation of a route based on a rule by the safety function section 300.

The safety function section 300 has a function of assuming a possibility that a determination or processing (hereinafter simply referred to as deviant processing) departing from a particular allowable range is derived from deep learning in the primary arithmetic section 200 and monitoring such deviant processing.

For example, the safety function section 300 is configured to (1) recognize the external object (hereinafter may be referred to as a target object) on the basis of a method for recognizing the target that is conventionally adopted for the automobile and the like, and (2) set a safe area through which the vehicle can travel safely by using a method that is conventionally adopted for the automobile and the like, and set a route that runs through such a safe area as the travel route on which the automobile should travel.

More specifically, the safety function section 300 includes an object recognition section 301 that recognizes the external object, a classification section 302, a preprocessing section 303, a free space search section 304, and a route creation section 305.

The object recognition section 301 recognizes the external object on the basis of: the image (including the video) of the outside of the vehicle that is captured by the external camera 11; and a peak list of reflected waves detected by the radar 12.

The classification section 302 and the preprocessing section 303 may not execute deep learning or the like, but may estimate the external environment by a rule-based method based on a specified rule on the basis of a recognition result of the object recognition section 301. More specifically, the classification section 302 receives the object recognition result from the object recognition section 301, and classifies the recognized objects as one of a mobile object and a stationary object. Further specifically, in the classification section 302, (1) the surroundings of the host vehicle are divided into the plural areas (for example, the front, the right, the left, and the rear), (2) object information recognized by the external camera 11 and object information recognized by the radar 12 are integrated for each of the areas, and (3) classified information of the mobile object and the stationary object in each of the areas is generated.

The preprocessing section 303 integrates a classification result for each of the areas that is generated in the classification section 302. The integrated information is managed, for example, as the classification information of the mobile object and the stationary object around the host vehicle, on a grid map, and the like. In addition, the preprocessing section 303 predicts a distance between the mobile object and the host vehicle as well as a direction and a relative speed of the mobile object, and integrates results thereof as attached information of the mobile object. Furthermore, the preprocessing section 303 combines the high-precision map information that is acquired from the inside or the outside of the automobile, the location information, the vehicle speed information, the six-axis information, and the like to estimate the location of the host vehicle with respect to the mobile object/the stationary object.

The free space search section 304 searches for the free space where a collision with the mobile object/the stationary object (hereinafter also referred to as the target object), the location of which is estimated by the preprocessing section 303, can be avoided. For example, the free space search section 304 sets the free space on the basis of such a specified rule that an area located a few meters from the target object is regarded as an unavoidable area. In the case where the target object is the mobile object, the free space search section 304 sets the free space in consideration of a movement speed. For example, the free space is an area that is on a road and where a mobile obstacle such as another vehicle or the pedestrian and a stationary obstacle such as the median strip or the center poll do not exist. The free space may include a space on a road shoulder where an emergency vehicle can be parked.

The route creation section 305 calculates such a route that runs through the free space searched by the free space search section 304. Although a calculation method of the route by the route creation section 305 is not particularly limited, for example, the plural routes running through the free space are created, and the route with the lowest route cost is selected from the plural routes. The route that is calculated by the route creation section 305 is output to a target motion decision section 214, which will be described later.

The functions of the safety function section 300 that have been described above are implemented by setting rules of the recognition method of the target and an avoidance method thereof, which are conventionally adopted for the automobile and the like.

—1-3. Primary Arithmetic Section (2)—

In addition to the block described in above "1-1. Primary arithmetic section (1)", the primary arithmetic section 200 includes a danger state determination section 210, a first vehicle model 211, a second vehicle model 212, a route decision section 213, the target motion decision section 214, a vehicle motion energy setting section 215, an energy management section 216, a driver operation recognition section 217, an image processing section 218, and a selector 220. The image processing section 218 executes specified image processing on the image that is captured by the internal camera 17.

In the case where the danger state determination section 210 determines that the collision with the target object or the departure from the lane possibly occurs on the basis of the external environment model 204, the danger state determination section 210 sets a travel route (for example, the target location and the vehicle speed) to avoid the collision with the target object or the departure from the lane.

The driver operation recognition section 217 recognizes the operation amount and an operation direction by the driver as information used to decide the travel route. More specifically, the driver operation recognition section 217 recognizes the operation amount and the operation direction by the driver on the basis of the output of the driver input section 16, and outputs a recognition result to the route decision section 213.

The route decision section 213 decides the vehicle travel route on the basis of the travel route set by the route creation section 206, the travel route set by the route creation section 305 in the safety function section 300, and the recognition result of the driver operation recognition section 217. Although a method for deciding this travel route is not particularly limited, for example, during the normal travel, the route decision section 213 may make the travel route set by the route creation section 206 a top priority. Alternatively, in the case where the travel route set by the route creation section 206 does not run through the free space searched by the free space search section 304, the route decision section 213 may select the travel route set by the route creation section 305 in the safety function section 300. Further alternatively, according to the operation amount or the operation direction by the driver, the route decision section 213 may adjust the selected travel route or prioritizes the operation by the driver.

The target motion decision section 214 decides target six-axis motion (for example, acceleration, an angular speed, and the like) with respect to the travel route decided by the route decision section 213, for example. When deciding the target six-axis motion, the target motion decision section 214 may use the specified first vehicle model 211. A six-axis vehicle model is created by modeling acceleration in three-axis directions of "front-rear", "right-left", and "up-down" of the traveling vehicle and angular speeds in three-axis directions of "pitch", "roll", and "yaw". That is, instead of acknowledging motion of the vehicle on a plane (only in the front-rear/right-left direction (movement in X-Y) and yaw motion (Z-axis) of the vehicle), which has been practiced in the traditional vehicle motion engineering, the six-axis vehicle model is created as a numerical model that replicates behavior of the vehicle by using a total of the six axes that include pitching (Y-axis), rolling (X-axis) motion, and movement in the Z-axis (vertical motion of a vehicle body) of a vehicle body placed on four wheels via suspensions. The first vehicle model 211 is created on the basis of a basic motor function of the vehicle, which is set in advance, the interior/exterior environment information of the vehicle, and the like, for example, and is appropriately updated.

The vehicle motion energy setting section 215 calculates torque that is requested to each of a drive system, a steering system, and a brake system in regard to the target six-axis motion decided by the target motion decision section 214. For example, the drive system includes an engine system, a motor, and the transmission. For example, the steering system includes the steering wheel. For example, the brake system includes the brake.

The energy management section 216 calculates a control amount of the actuators AC to obtain the highest energy efficiency at the time when the target motion decided by the target motion decision section 214 is achieved. More specifically exemplified, the energy management section 216 calculates opening/closing timing of intake/exhaust valves, fuel injection timing of an injector, and the like that improve the fuel economy the most in order to achieve energy torque decided by the target motion decision section 214. When performing energy management, the energy management section 216 may use the specified second vehicle model 212. The second vehicle model 212 is a model that represents energy consumption of the vehicle. More specifically, the second vehicle model 212 is a model that represents the fuel economy and electric consumption for the operation of the actuators AC in the vehicle. In detail, the second vehicle model 212 is created by modeling the opening/closing timing of the intake/exhaust valves, the fuel injection timing of the injector, valve opening/closing timing of an exhaust recirculation system, and the like that improve the fuel economy the most when a specified amount of the engine torque is output, for example. The second vehicle model is created during the travel of the vehicle, for example, and is appropriately updated.

As described above, in this embodiment, the automated driving system CU acknowledges the host vehicle, the external environment, and the driver state so as to execute the virtual driving in parallel with driving of the automobile by the driver. In the case where the automated driving system CU acknowledges the driver state and determines that the dysfunction or the illness has occurred to the driver, the automated driving system CU actuates the actuators AC for operating the automobile on the basis of the output from the vehicle motion energy setting section 215 and the energy management section 216 described above.

Such switching operation can be realized by the above-described configuration for automated driving, a driver state recognition section 400, an automated driving switching section 410, and the selector 220.

The driver state recognition section 400 recognizes the driver state on the basis of the information acquired by the information acquisition means 10, the processing result in each of the above-described blocks, and the like. Then, the driver state recognition section 400 acknowledges the states of the high voluntary function, the low voluntary function, and the involuntary function on the basis of the recognition result. For example, the driver state recognition section 400 recognizes the driver state on the basis of the results recognized by the object recognition sections 201, 301 and the driver operation recognition section 217, the image capturing information by the internal camera 17 (the image processing result of the image processing section 218), the output information from the external environment estimation section 203, and/or the like. In FIG. 5B, the driver state recognition section 400 receives the output from the pre-processing section 303, the driver operation recognition section 217, the image processing section 218, and the external environment estimation section 203. However, embodiments are not limited thereto. The driver state recognition section 400 may recognize the states of the high voluntary function, the low voluntary function, and the involuntary function on the basis of the information from other sections.

As illustrated in FIG. 5B, the driver state recognition section 400 includes a high voluntary function recognition section 401, a low voluntary function recognition section 402, and an involuntary function recognition section 403.

The high voluntary function recognition section 401 recognizes whether the high voluntary function of the driver works normally. More specifically, the high voluntary function recognition section 401 checks whether the operation based on the high voluntary function of the driver is performed on the basis of the external environment estimated by the external environment estimation section 203, an operating status of the accelerator pedal or the steering wheel recognized by the driver operation recognition section 217, and the output from the mechanical sensor 15, for example. Further specifically, the high voluntary function recognition section 401 recognizes how the driver acts when the driver passes a location such as a corner or an intersection where a person possibly and suddenly runs in front of the driver. As a result of a demonstration experiment, the inventor has acquired such knowledge that the driver decelerates the vehicle to secure safety as approaching the corner or the intersection in the case where the high voluntary function works normally, that is, in the healthy state. In contrast, the driver drives through the corner or the intersection without deceleration in the case where the driver suffers from a symptom of apoplexy and thus an anticipation function of the driver is lost. According to the knowledge acquired by the inventor, the driver in such a state may travel on an usually empty road by tracing a lane, e.g., following lane lines. Traveling by tracing the lane relates to the voluntary function that can be processed even when close to unconsciousness, and belongs to the low voluntary function in the classification by the inventor. In other words, the low voluntary function may work normally even when the high voluntary function has declined.

Accordingly, the high voluntary function recognition section 401 determines whether the driving operation that corresponds to the location where the driver passes through, in particular, the driving action with the assumption of a prediction of danger, so-called "driving while forecasting possible occurrence of something" is executed normally on the basis of the recognition result and/or the detection result of the external environment estimation section 203, the driver operation recognition section 217, and/or the mechanical sensor 15 described above. Whether a travel environment is an environment that requires the automobile to perform "driving while forecasting possible occurrence of something", may be determined, e.g., by quantifying map information (for example, the target information such as building information) acquired from the GPS or the like and travel risk information of each of the targets. Then, the high voluntary function recognition section 401 recognizes that the high voluntary function does not work normally in the case where the driver continues performing rapid operations such as rapid depression of the accelerator pedal and rapid turning of the steering wheel regardless of a fact that the travel risk is increased. Alternatively, the high voluntary function recognition section 401 may recognize whether the high voluntary function works normally on the basis of motion of the line of sight of the driver such as the saccade reaction against saliency or movement of the line of sight to a figure if present. Further alternatively, with the assumption of combination with the other indices, the high voluntary function recognition section 401 may count the number of checking of an internal camera mirror, and may use the extremely small number of checking of the mirror or a significant reduction in the number for the recognition of the high voluntary function. In addition, as described above, in a situation where the high voluntary function does not work normally, changes may occur to an autonomic system of the driver. Thus, such an autonomic system (e.g., a heart rate) may be monitored in order to confirm a change in the high voluntary function.

In general, it is more difficult to recognize the high voluntary function than the low voluntary function and the involuntary function. Accordingly, the high voluntary function recognition section 401 (1) may recognize that the high voluntary function does not work normally by combining plural indices, or (2) may cause an actuation execution section 50 to execute actuation for the driver so as to check reaction of the driver and recognize that the high voluntary function does not work normally on the basis of the result in the case where it is estimated that the high voluntary function does not work normally. Although a configuration of the actuation execution section 50 is not particularly limited, a dedicated device may be provided therefor. Alternatively, a screen of a car navigation system or a head-up display or a sound producing device such as a horn or a speaker may be used. The high voluntary function recognition section 401 is an example of the voluntary function recognition section.

The low voluntary function recognition section 402 recognizes whether the low voluntary function works normally. More specifically, the low voluntary function recognition section 402 acknowledges presence or absence of wobbling of steering or instability of the speed from the results recognized by the object recognition sections 201, 301 and the driver operation recognition section 217, for example, so as to check whether the operation based on the low voluntary function of the driver is performed. Further specifically, for example, the low voluntary function recognition section 402 checks whether the travel of the automobile on the lane wobbles on the basis of the results recognized by the object recognition sections 201, 301 and the driver operation recognition section 217. The low voluntary function recognition section 402 also recognizes whether the driver performs such travel that a distance between the host vehicle and a forward vehicle is repeatedly reduced and increased. Furthermore, as described above, the low voluntary function recognition section 402 checks whether vestibulo-ocular reflex is normal, that is, whether the constancy of the head is maintained on the basis of the image capturing result of the internal camera 17. For example, the low voluntary function recognition section 402 analyzes the motion of the head of the driver and motion of the line of sight of the driver on the basis of the video captured by the internal camera 17, so as to check whether vestibulo-ocular reflex is normal. Moreover, the low voluntary function recognition section 402 analyzes a degree of rocking of the head of the driver with respect to rocking of the automobile on the basis of the output from the mechanical sensor 15 and the video captured by the internal camera 17, so as to check whether the constancy of the head is maintained. The low voluntary function recognition section 402 is an example of the voluntary function recognition section.

The involuntary function recognition section 403 recognizes whether the involuntary function works normally on the basis of a fact that the involuntary function remains in the abnormal state for a specified time or longer. For example, the involuntary function recognition section 403 analyzes the imbalance driving posture of the driver and the eye opening amount of the driver on the basis of the image capturing result of the internal camera 17, so as to determine the outbreak of the illness of the driver. More specifically, the involuntary function recognition section 403 recognizes the outbreak of the illness of the driver, for example, in the case where an imbalance state of the driving posture of the driver and/or the eye opening/closing state of the driver continues for more than a predetermined period of time, e.g., two seconds.

When recognizing the outbreak of the illness of the driver, the driver state recognition section 400 outputs a recognition result to the automated driving switching section 410.

The automated driving switching section 410 outputs a control signal to the selector 220 on the basis of the output from the driver state recognition section 400.

The selector 220 has a function of switching whether or not to actually transmit the control signal for the virtual driving, which is calculated by the automated driving system CU, to the actuators AC. The selector 220 receives the control signals for actuating the actuators AC from the vehicle motion energy setting section 215 and the energy management section 216. The selector 220 is configured not to output the control signal for the virtual driving during the normal operation, that is, in the case where the driver is in the state capable of driving normally. Meanwhile, in the case where the driver state recognition section 400 recognizes the abnormality such as the illness of the driver, the selector 220 receives the control signal from the automated driving switching section 410 and outputs the control signal (hereinafter referred to as an automated driving control signal) for actuating the actuators AC from the vehicle motion energy setting section 215 and the energy management section 216. In each of the actuators AC (including an ECU that operates the actuators), when the automated driving control signal is output from the selector 220, automated driving that is based on the automated driving control signal is adopted instead of driving based on the operation signal from the driver.

As described above, according to the configuration in this embodiment, in the case where the driver state recognition section 400 recognizes the outbreak of the illness of the driver, the automated driving switching section 410 is notified of the recognition result, and the automated driving switching section 410 controls the selector 220. In this way, it is possible to operate the host vehicle instead of the driver in the manner to secure the safety of the host vehicle and the surroundings and to complement the declined function among the functions of the perception, the determination, and the operation of the driver.

Here, the technique of the present application is characterized in a point of reducing a determination time for the final driver abnormality determination by using the driver state recognition section 400 to detect the high voluntary function, the low voluntary function, and the involuntary function of the driver during driving and by combining the normal/abnormal determinations of the functions.

Figure 6:
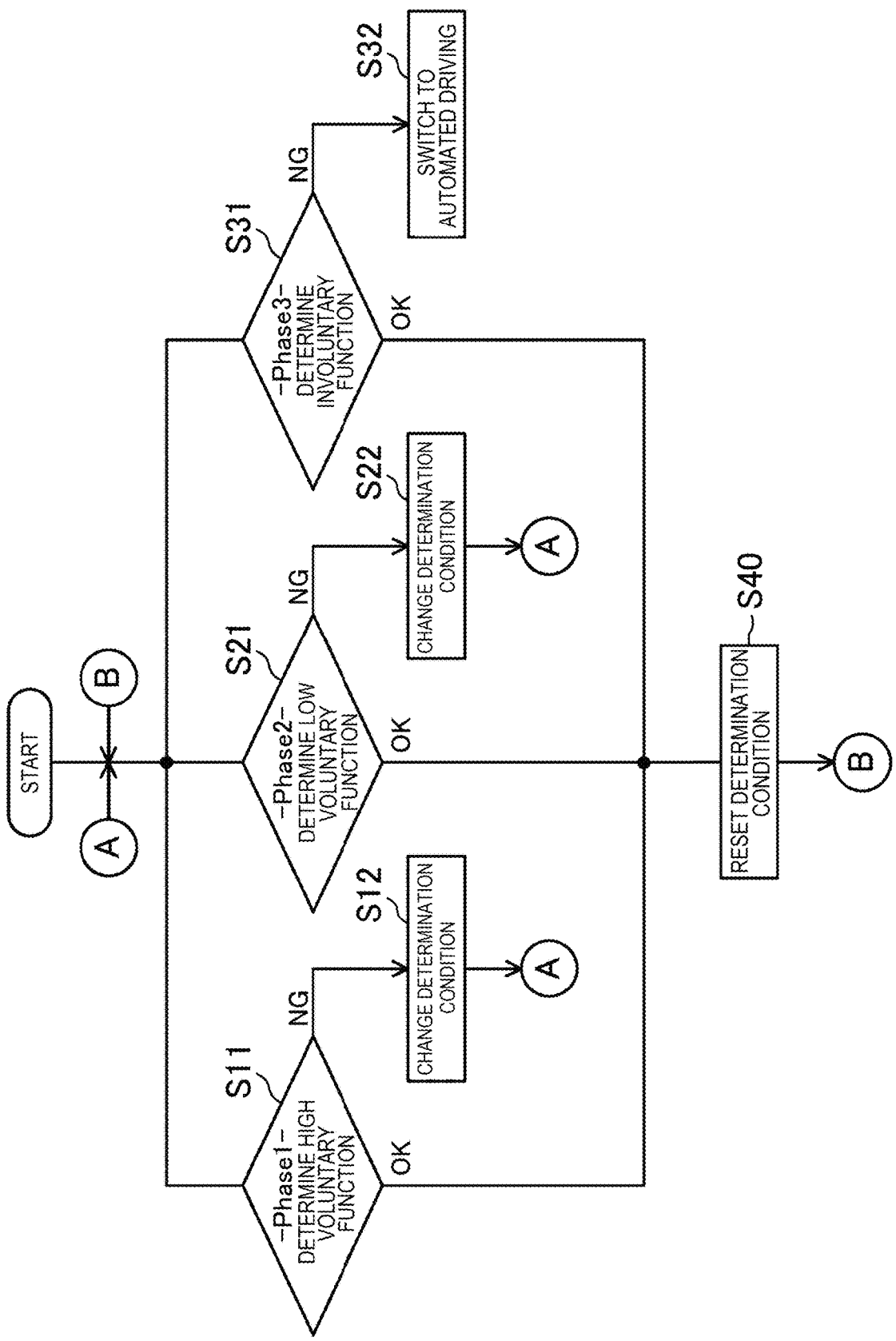
FIG. 6 is a flowchart illustrating exemplary operation of a driver state determination apparatus.

A specific description will hereinafter be made with reference to FIGS. 6 and 7. FIG. 6 is a flowchart illustrating an example of the operation of the driver state determination apparatus, and FIG. 7 is a table for illustrating the operation of the driver state determination apparatus.

As illustrated in FIG. 3, there is a case where the illness of the driver is shifted stepwise such that the abnormality is found in the high voluntary function as Phase 1, the abnormality is found in the low voluntary function as Phase 2, and the abnormality is found in the involuntary function as Phase 3. There is also a case where the abnormality is found in the involuntary function immediately after the outbreak of the illness of the driver. Furthermore, there is a case where the abnormality is found in the low voluntary function at first and then the abnormality is found in the involuntary function.

For the above reason, in FIG. 6, the abnormality determination of the high voluntary function (Phase 1), the abnormality determination of the low voluntary function (Phase 2), and the abnormality determination of the involuntary function (Phase 3) are processed in parallel.

In step S11, it is determined whether the high voluntary function works normally. In step S21, it is determined whether the low voluntary function works normally. In step S31, it is determined whether the involuntary function works normally.

Case 1 in FIG. 7 illustrates an example of the case where it is recognized that the high voluntary function works normally and that the low voluntary function works normally. That is, Case 1 in FIG. 7 illustrates the example of the case where the determinations in step S11 and step S21 are OK. At this time, for a determination in step S31, settings in a default state are used. For example, in the case where the abnormal state of the involuntary function continues for a specified determination time, the involuntary function recognition section 403 determines that the involuntary function is abnormal. Although the specified determination time is not particularly limited, an example in which the specified determination time is two seconds is illustrated in FIG. 7. In the case of the configuration illustrated in FIG. 5B, when the driver state recognition section 400 recognizes the outbreak of the illness of the driver, the recognition result is output to the automated driving switching section 410. Then, the automated driving switching section 410 controls the selector 220 and sends the output of the automated driving system that has executed virtual driving to the actuators AC, so as to switch to automated driving.

Case 2 in FIG. 7 illustrates an example of the case where it is recognized that the high voluntary function works normally and that the low voluntary function does not work normally. That is, Case 2 in FIG. 7 illustrates the example of the case where the determination in step S11 is OK and the determination in step S21 is NG. At this time, the involuntary function recognition section 403 reduces the determination time that is required to recognize whether the involuntary function works normally. An example in which the determination time is reduced from two seconds to one second is illustrated in FIG. 7. In this way, in the case where the abnormality of the involuntary function of the driver continues for one second, the involuntary function recognition section 403 determines that the involuntary function is abnormal.

Case 3 in FIG. 7 illustrates an example of the case where it is recognized that the high voluntary function does not work normally. That is, Case 3 in FIG. 7 illustrates the example of the case where the determination in step S11 is NG. In this case, in step S12, for example, the low voluntary function recognition section 402 changes a determination condition used to determine whether the low voluntary function works normally. In an example illustrated in FIG. 7, the low voluntary function recognition section 402 reduces a threshold used to determine the abnormality of the low voluntary function so as to promote the determination of the abnormality. Furthermore, if the determination in step S21 is NG, in step S22, the involuntary function recognition section 403 reduces the determination time that is required to recognize whether the involuntary function works normally. An example in which the determination time is reduced to 0.5 second is illustrated in FIG. 7. If the determination in step S11 is NG, the determination conditions may be changed for both of the low voluntary function recognition section 402 and the involuntary function recognition section 403. For example, the threshold for the low voluntary function recognition section 402 may be reduced, and the determination time by the involuntary function recognition section 403 may be reduced to one second. Here, the change of the determination condition for the abnormality of the low voluntary function is not limited to the reduction of the threshold. For example, accuracy of the determination criterion or the determination threshold used to detect the abnormality of the driver may be increased. In this way, it is possible to substantially reduce the time required for the abnormality determination and to increase the accuracy of the abnormality determination.

As it has been described so far, according to this embodiment, the voluntary function recognition sections (the high voluntary function recognition section 401 and the low voluntary function recognition section 402) are provided to each recognize whether the voluntary function works normally. Then, in the case where it is recognized that the voluntary function does not work normally, the determination time that is required to determine whether the involuntary function recognition section functions normally is reduced. That is, in this embodiment, the voluntary function recognition section detects the prediction before the outbreak of the driver abnormality. Then, in the case where the prediction is detected, the determination time that is required to determine whether the involuntary function recognition section functions normally is reduced. In this way, even in the case where the driving function of the driver is impaired due to the illness or the like, the driver abnormality determination can be accelerated. Therefore, it is possible to promptly and reliably execute safety control such as automated driving and automated stop.

In this embodiment, such knowledge is acquired that, in the case where the voluntary function is classified into the high voluntary function and the low voluntary function, after the outbreak of the driver abnormality, the high voluntary function is lost first, and the low voluntary function remains to the end. Thus, before the involuntary function is declined, the condition of the abnormality determination is changed, and the determination time is reduced according to the combination of normality/abnormality of the high voluntary function and the low voluntary function. As a result, it is possible to further accelerate the driver abnormality determination and to increase the accuracy of the prediction related to the abnormality determination.

In the present disclosure, in addition to a concept that the time required for the determination is directly reduced as illustrated in FIG. 7, the reduction of the time includes a concept that the time required for the abnormality determination is indirectly reduced by relaxing the threshold for the abnormality determination or increasing the accuracy of the determination threshold.

OTHER EMBODIMENTS

In the above embodiment, in the case where the determinations in steps S11 and S21 are NG, in steps S12 and S22, the determination condition (for example, the determination time) for each of the functions is thereafter changed. However, a step of resetting this changed determination condition may be provided. For example, in the case where the normal state is maintained for the specified time after the determination in step S11 and/or step S21 is NG, for example, in the case where a state with the determination of OK is maintained in steps S11, S21, and S31, the processing may proceed to step S40, and the determination condition for each of the functions may be reset to a default value.

In the above embodiment, in the flow illustrated in FIG. 6, the automated driving system CU may ask the driver a question such as "Are you OK?" or "Why don't you have a short break?" before and after changing the determination condition, and may change the processing according to the result. For example, in the case where the automated driving system CU asks the above question and receives a quick and appropriate response from the driver, the automated driving system CU may not change the determination condition in step S12 and/or step S22.

In this way, when the actuation such as asking the driver the question or warning the driver, it is possible to increase the accuracy of the driver abnormality determination and urge the driver to act safely.

The following description relates to a computer environment in which embodiments of the present disclosure may be implemented. This environment may include an embedded computer environment, local multi-processor embodiment, remote (e.g., cloud-based) environment, or a mixture of all the environments.

Figure 8:
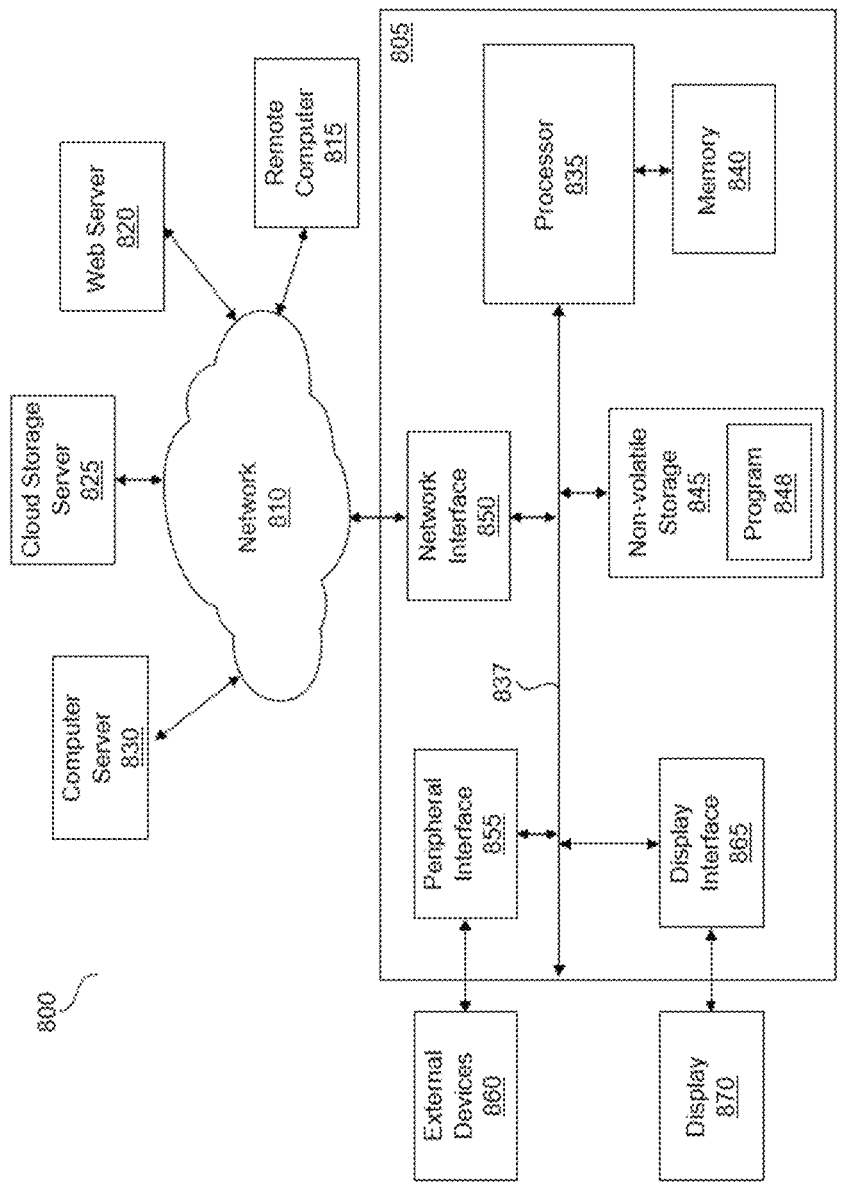
FIG. 8 is a block diagram of computer-based circuitry that may be used to implement control features of the present disclosure.

FIG. 8 illustrates a block diagram of a computer that may implement the various embodiments described herein. The present disclosure may be embodied as a system, a method, and/or a computer program product. The computer program product may include a computer readable storage medium on which computer readable program instructions are recorded that may cause one or more processors to carry out aspects of the embodiment.

The non-transitory computer readable storage medium may be a tangible device that can store instructions for use by an instruction execution device (processor). The computer readable storage medium may be, for example, but is not limited to, an electronic storage device, a magnetic storage device, an optical storage device, an electromagnetic storage device, a semiconductor storage device, or any appropriate combination of these devices. A non-exhaustive list of more specific examples of the computer readable storage medium includes each of the following (and appropriate combinations): flexible disk, hard disk, solid-state drive (SSD), random access memory (RAM), read-only memory (ROM), erasable programmable read-only memory (EPROM or Flash), static random access memory (SRAM), compact disc (CD or CD-ROM), digital versatile disk (DVD) and memory card or stick. A computer readable storage medium, as used in this disclosure, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described in this disclosure can be downloaded to an appropriate computing or processing device from a computer readable storage medium or to an external computer or external storage device via a global network (i.e., the Internet), a local area network, a wide area network and/or a wireless network. The network may include copper transmission wires, optical communication fibers, wireless transmission, routers, firewalls, switches, gateway computers and/or edge servers. A network adapter card or network interface in each computing or processing device may receive computer readable program instructions from the network and forward the computer readable program instructions for storage in a computer readable storage medium within the computing or processing device.

Computer readable program instructions for carrying out operations of the present disclosure may include machine language instructions and/or microcode, which may be compiled or interpreted from source code written in any combination of one or more programming languages, including assembly language, Basic, Fortran, Java, Python, R, C, C++, C# or similar programming languages. The computer readable program instructions may execute entirely on a user's personal computer, notebook computer, tablet, or smartphone, entirely on a remote computer or compute server, or any combination of these computing devices. The remote computer or compute server may be connected to the user's device or devices through a computer network, including a local area network or a wide area network, or a global network (i.e., the Internet). In some embodiments, electronic circuitry including, for example, programmable logic circuitry, field-programmable gate arrays (FPGA), or programmable logic arrays (PLA) may execute the computer readable program instructions by using information from the computer readable program instructions to configure or customize the electronic circuitry, in order to perform aspects of the present disclosure.

Aspects of the present disclosure are described herein with reference to flow diagrams and block diagrams of methods, apparatus (systems), and computer program products according to embodiments of the disclosure. It will be understood by those skilled in the art that each block of the flow diagrams and block diagrams, and combinations of blocks in the flow diagrams and block diagrams, can be implemented by computer readable program instructions.

The computer readable program instructions that may implement the systems and methods described in this disclosure may be provided to one or more processors (and/or one or more cores within a processor) of a general purpose computer, special purpose computer, or other programmable apparatus to produce a machine, such that the instructions, which execute via the processor of the computer or other programmable apparatus, create a system for implementing the functions specified in the flow diagrams and block diagrams in the present disclosure. These computer readable program instructions may also be stored in a computer readable storage medium that can direct a computer, a programmable apparatus, and/or other devices to function in a particular manner, such that the computer readable storage medium having stored instructions is an article of manufacture including instructions which implement aspects of the functions specified in the flow diagrams and block diagrams in the present disclosure.

The computer readable program instructions may also be loaded onto a computer, other programmable apparatus, or other device to cause a series of operational steps to be performed on the computer, other programmable apparatus or other device to produce a computer implemented process, such that the instructions which execute on the computer, other programmable apparatus, or other device implement the functions specified in the flow diagrams and block diagrams in the present disclosure.

FIG. 8 is a functional block diagram illustrating a networked system 800 of one or more networked computers and servers. In an embodiment, the hardware and software environment illustrated in FIG. 8 may provide an exemplary platform for implementation of the software and/or methods according to the present disclosure.

Referring to FIG. 8, a networked system 800 may include, but is not limited to, computer 805, network 810, remote computer 815, web server 820, cloud storage server 825 and computer server 830. In some embodiments, multiple instances of one or more of the functional blocks illustrated in FIG. 8 may be employed.

Additional detail of computer 805 is shown in FIG. 8. The functional blocks illustrated within computer 805 are provided only to establish exemplary functionality and are not intended to be exhaustive. And while details are not provided for remote computer 815, web server 820, cloud storage server 825 and compute server 830, these other computers and devices may include similar functionality to that shown for computer 805.

Computer 805 may be built into the automobile, a personal computer (PC), a desktop computer, laptop computer, tablet computer, netbook computer, a personal digital assistant (PDA), a smart phone, or any other programmable electronic device capable of communicating with other devices on network 810.

Computer 805 may include processor 835, bus 837, memory 840, non-volatile storage 845, network interface 850, peripheral interface 855 and display interface 865. Each of these functions may be implemented, in some embodiments, as individual electronic subsystems (integrated circuit chip or combination of chips and associated devices), or, in other embodiments, some combination of functions may be implemented on a single chip (sometimes called a system on chip or SoC).

Processor 835 may be one or more single or multi-chip microprocessors, such as those designed and/or manufactured by Intel Corporation, Advanced Micro Devices, Inc. (AMD), Arm Holdings (Arm), Apple Computer, etc. Examples of microprocessors include Celeron, Pentium, Core i3, Core i5 and Core i7 from Intel Corporation; Opteron, Phenom, Athlon, Turion and Ryzen from AMD; and Cortex-A, Cortex-R and Cortex-M from Arm.

Bus 837 may be a proprietary or industry standard high-speed parallel or serial peripheral interconnect bus, such as ISA, PCI, PCI Express (PCI-e), AGP, and the like.

Memory 840 and non-volatile storage 845 may be computer-readable storage media. Memory 840 may include any suitable volatile storage devices such as Dynamic Random Access Memory (DRAM) and Static Random Access Memory (SRAM). Non-volatile storage 845 may include one or more of the following: flexible disk, hard disk, solid-state drive (SSD), read-only memory (ROM), erasable programmable read-only memory (EPROM or Flash), compact disc (CD or CD-ROM), digital versatile disk (DVD) and memory card or stick.

Program 848 may be a collection of machine readable instructions and/or data that is stored in non-volatile storage 845 and is used to create, manage and control certain software functions that are discussed in detail elsewhere in the present disclosure and illustrated in the drawings. In some embodiments, memory 840 may be considerably faster than non-volatile storage 845. In such embodiments, program 848 may be transferred from non-volatile storage 845 to memory 840 prior to execution by processor 835.

Computer 805 may be capable of communicating and interacting with other computers via network 810 through network interface 850. Network 810 may be, for example, a local area network (LAN), a wide area network (WAN) such as the Internet, or a combination of the two, and may include wired, wireless, or fiber optic connections. In general, network 810 can be any combination of connections and protocols that support communications between two or more computers and related devices.

Peripheral interface 855 may allow for input and output of data with other devices that may be connected locally with computer 805. For example, peripheral interface 855 may provide a connection to external devices 860. External devices 860 may include input devices, e.g., any or all of the devices in the information acquisition means 10 and/or other suitable input devices, and output devices, e.g., any or all of the various actuator devices AC and/or other suitable output devices, e.g., a speaker. External devices 860 may also include portable computer-readable storage media such as, for example, thumb drives, portable optical or magnetic disks, and memory cards. Software and data used to practice embodiments of the present disclosure, for example, program 848, may be stored on such portable computer-readable storage media. In such embodiments, software may be loaded onto non-volatile storage 845 or, alternatively, directly into memory 840 via peripheral interface 855. Peripheral interface 855 may use an industry standard connection, such as RS-232 or Universal Serial Bus (USB), to connect with external devices 860.

Display interface 865 may connect computer 805 to display 870, e.g., a head-up display or a screen of a car navigation system. Display 870 may be used, in some embodiments, to present a command line or graphical user interface to a user of computer 805. Display interface 865 may connect to display 870 using one or more proprietary or industry standard connections, such as VGA, DVI, DisplayPort and HDMI.

As described above, network interface 850, provides for communications with other computing and storage systems or devices external to computer 805. Software programs and data discussed herein may be downloaded from, for example, remote computer 815, web server 820, cloud storage server 825 and compute server 830 to non-volatile storage 845 through network interface 850 and network 810. Furthermore, the systems and methods described in this disclosure may be executed by one or more computers connected to computer 805 through network interface 850 and network 810. For example, in some embodiments the systems and methods described in this disclosure may be executed by remote computer 815, computer server 830, or a combination of the interconnected computers on network 810.

Data, datasets and/or databases employed in embodiments of the systems and methods described in this disclosure may be stored and or downloaded from remote computer 815, web server 820, cloud storage server 825 and compute server 830.

The invention claimed is:

1. A driver state determination apparatus for use in an automobile, the driver state determination apparatus comprising:
circuitry configured to:
recognize whether a first voluntary function of the driver works normally, including
estimate saliency or motion in an external environment;
detect a line of sight of the driver;
determine whether the line of sight of the driver follows the saliency or motion, wherein, on condition that the light of sight does not follow the saliency or motion, determine that the first voluntary function is not working normally;
recognize whether a second voluntary function of the driver, which is a lower voluntary function than the first voluntary function, works normally; and
recognize that an involuntary function of the driver does not work normally on condition that the involuntary function remains in an abnormal state for at least a specified time, wherein
on condition that the first voluntary function does not work normally, change determination criteria for recognition of the second voluntary function and/or the specified time required for the involuntary function recognition, and
on condition that the second voluntary function does not work normally, change the specified time for the involuntary function recognition.

2. The driver state determination apparatus according to claim 1, wherein the circuitry is further configured to recognize whether the first voluntary function of the driver works normally by:
estimate the external environment;
recognize an operating status of actuators in the vehicle;
determine a speed of the automobile; and
check whether the driver decelerates the vehicle when approaching a corner or an intersection based on the external environment, the operating status and the speed of the automobile, wherein
on condition that one of these conditions is not met, determine that the first voluntary function is not working normally.

3. The driver state determination apparatus according to claim 1, wherein the circuitry is further configured to:
check whether steering of the automobile is wobbling or whether speed of the automobile is unstable, wherein,
on condition that one of these conditions is met, determine that the second voluntary function is not working normally.

4. The driver state determination apparatus according to claim 1, wherein the circuitry is further configured to:
determine whether vestibulo-ocular reflex is normal, and, if not, determine that the second voluntary function is not working normally.

5. The driver state determination apparatus according to claim 1, wherein the circuitry is further configured to:
on condition that the first voluntary function is not working normally, reduce a threshold used to determine the abnormality of the second voluntary function.

6. The driver state determination apparatus according to claim 1, wherein the circuitry is further configured to:
on condition that at least one of the first voluntary function and the second voluntary function does not work normally, output automated driving control signals to actuators in the vehicle.

7. The driver state determination apparatus according to claim 6, wherein the circuitry is further configured to, before outputting automated driving control signals, orally or visually give the driver a warning.

8. The driver state determination apparatus according to claim 7, on condition that the driver makes an appropriate response to the warning, the circuitry is further configured to refrain from outputting automated driving control signals.

9. The driver state determination apparatus according to claim 6, wherein the circuitry is further configured to, after outputting control signals, orally or visually give the driver a warning.

10. The driver state determination apparatus according to claim 1, wherein the specified time for the involuntary function recognition when the first voluntary function is not working normally is less than when the only second voluntary function is not working normally.

11. A driver state control determination method for a driver in a vehicle, the method comprising:
recognizing whether a first voluntary function of the driver works normally, including
estimating saliency or motion in an external environment;
detecting a line of sight of the driver;
determining whether the line of sight of the driver follows the saliency or motion, wherein, on condition that the light of sight does not follow the saliency or motion, determine that the first voluntary function is not working normally;
recognizing whether a second voluntary function of the driver, which is a lower voluntary function than the first voluntary function, works normally; and
recognizing that an involuntary function of the driver does not work normally on condition that the involuntary function remains in an abnormal state for at least a specified time, wherein
on condition that the first voluntary function does not work normally, changing determination criteria for recognition of the second voluntary function and/or the specified time required for the involuntary function recognition, and
on condition that the second voluntary function does not work normally, change the specified time for the involuntary function recognition.

12. The method according to claim 11, further comprising:
on condition that at least one of the first voluntary function and the second voluntary function does not work normally, output automated driving control signals to actuators in the vehicle.

13. A non-transitory computer readable storage including computer readable instructions that when executed by a controller cause the controller to execute a driver state determination method for a driver in a vehicle, the method comprising:
recognizing whether a first voluntary function of the driver works normally, including
estimating saliency or motion in an external environment;
detecting a line of sight of the driver;
determining whether the line of sight of the driver follows the saliency or motion, wherein, on condition that the light of sight does not follow the saliency or motion, determine that the first voluntary function is not working normally;

recognizing whether a second voluntary function of the driver, which is a lower voluntary function than the first voluntary function, works normally; and recognizing that an involuntary function of the driver does not work normally on condition that the involuntary function remains in an abnormal state for at least a specified time, wherein on condition that the first voluntary function does not work normally, changing determination criteria for recognition of the second voluntary function and/or the specified time required for the involuntary function recognition, and on condition that the second voluntary function does not work normally, change the specified time for the involuntary function recognition.

14. The method according to claim 13, further comprising:

on condition that at least one of the first voluntary function and the second voluntary function does not work normally, output automated driving control signals to actuators in the vehicle.

15. The method according to claim 13, further comprising recognizing whether the first voluntary function of the driver works normally, further includes:

estimating the external environment;

recognizing an operating status of actuators in the vehicle;

determining a speed of the automobile; and checking whether the driver decelerates the vehicle when approaching a corner or an intersection based on the external environment, the operating status and the speed of the automobile, wherein on condition that one of these conditions is not met, determining that the first voluntary function is not working normally.

16. The method according to claim 11, further comprising recognizing whether the first voluntary function of the driver works normally further includes:

estimating the external environment;

recognizing an operating status of actuators in the vehicle;

determining a speed of the automobile; and checking whether the driver decelerates the vehicle when approaching a corner or an intersection based on the external environment, the operating status and the speed of the automobile, wherein on condition that one of these conditions is not met, determining that the first voluntary function is not working normally.

* * * * *